(12) United States Patent
Ramos et al.

(10) Patent No.: US 9,974,679 B2
(45) Date of Patent: *May 22, 2018

(54) STENT DELIVERY SYSTEM

(71) Applicant: BOSTON SCIENTIFIC SCIMED, INC., Maple Grove, MN (US)

(72) Inventors: Tim Ramos, Blaine, MN (US); Gerald W. Grabowski, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 153 days.

This patent is subject to a terminal disclaimer.

(21) Appl. No.: 14/968,026

(22) Filed: Dec. 14, 2015

(65) Prior Publication Data

US 2016/0095729 A1    Apr. 7, 2016

Related U.S. Application Data

(63) Continuation of application No. 13/240,765, filed on Sep. 22, 2011, now Pat. No. 9,220,619.
(Continued)

(51) Int. Cl.
*A61F 2/06* (2013.01)
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC .......................... A61F 2/966; A61F 2002/9517
See application file for complete search history.

(56) References Cited

U.S. PATENT DOCUMENTS 3,613,684 A    10/1971   Sheridan
4,665,918 A    5/1987    Garza et al.
(Continued)

FOREIGN PATENT DOCUMENTS

EP    0676936 A1    10/1995
EP    0684022 A2    11/1995
(Continued)

OTHER PUBLICATIONS

All non-patent literature documents and foreign patent documents have been previously uploaded in parent U.S. Appl. No. 13/240,765, filed Dec. 29, 2015.

*Primary Examiner* — Richard Louis
(74) *Attorney, Agent, or Firm* — Seager, Tufte & Wickhem, LLP

(57) ABSTRACT

Stent delivery systems and methods for making and using the same are disclosed. An example stent delivery system may include an inner member having a proximal end. A sleeve may be coupled to the inner member adjacent to the proximal end. A deployment sheath may be disposed about the inner member. A gear rack assembly may be coupled to the deployment sheath. A stent may be disposed between the inner member and the deployment sheath. A handle may be coupled to the inner member and to the deployment sheath. The handle may include an actuation member. The actuation member may be coupled to the gear rack assembly so that actuation of the actuation to member shifts the longitudinal position of the gear rack assembly and the deployment sheath. An engagement mechanism may be coupled to the gear rack assembly. The engagement mechanism may be configured to engage the sleeve of the inner member so that proximal retraction of the gear rack assembly results in proximal retraction of the inner shaft.

18 Claims, 16 Drawing Sheets

Related U.S. Application Data

(60) Provisional application No. 61/414,858, filed on Nov. 17, 2010.

(56) References Cited

U.S. PATENT DOCUMENTS

| | | |
|---|---|---|
| 4,732,152 A | 3/1988 | Wallstén et al. |
| 4,906,232 A | 3/1990 | Reynolds |
| 5,026,377 A | 6/1991 | Burton et al. |
| 5,071,407 A | 12/1991 | Termin et al. |
| 5,158,548 A | 10/1992 | Lau et al. |
| 5,163,905 A | 11/1992 | Don Michael |
| 5,201,757 A | 4/1993 | Heyn et al. |
| 5,221,261 A | 6/1993 | Termin et al. |
| 5,238,004 A | 8/1993 | Sahatjian et al. |
| 5,346,471 A | 9/1994 | Raulerson |
| 5,378,239 A | 1/1995 | Termin et al. |
| 5,433,723 A | 7/1995 | Lindenberg et al. |
| 5,443,907 A | 8/1995 | Slaikeu et al. |
| 5,445,646 A | 8/1995 | Euteneuer et al. |
| 5,496,277 A | 3/1996 | Termin et al. |
| 5,534,007 A | 7/1996 | St. Germain et al. |
| 5,571,135 A | 11/1996 | Fraser et al. |
| 5,662,703 A | 9/1997 | Yurek et al. |
| 5,674,242 A | 10/1997 | Phan et al. |
| 5,690,644 A | 11/1997 | Yurek et al. |
| 5,695,499 A | 12/1997 | Helgerson et al. |
| 5,702,364 A | 12/1997 | Euteneuer et al. |
| 5,707,376 A | 1/1998 | Kavteladze et al. |
| 5,713,860 A | 2/1998 | Kaplan et al. |
| 5,733,267 A | 3/1998 | Del Toro |
| 5,755,777 A | 5/1998 | Chuter |
| 5,772,609 A | 6/1998 | Nguyen et al. |
| 5,772,669 A | 6/1998 | Vrba |
| 5,788,707 A | 8/1998 | Del Toro et al. |
| 5,830,181 A | 11/1998 | Thornton |
| 5,833,694 A | 11/1998 | Poncet |
| 5,833,706 A | 11/1998 | St. Germain et al. |
| 5,843,090 A | 12/1998 | Schuetz |
| 5,843,091 A | 12/1998 | Holsinger et al. |
| 5,882,347 A | 3/1999 | Mouris-Laan et al. |
| 5,891,154 A | 4/1999 | Loeffler |
| 5,906,619 A | 5/1999 | Olson et al. |
| 5,954,764 A | 9/1999 | Parodi |
| 5,957,930 A | 9/1999 | Vrba |
| 5,980,483 A | 11/1999 | Dimitri |
| 6,017,577 A | 1/2000 | Hostettler et al. |
| 6,019,778 A | 2/2000 | Wilson et al. |
| 6,033,413 A | 3/2000 | Mikus et al. |
| 6,059,813 A | 5/2000 | Vrba et al. |
| 6,117,140 A | 9/2000 | Munsinger |
| 6,120,522 A | 9/2000 | Vrba et al. |
| 6,123,723 A | 9/2000 | Kónya et al. |
| 6,139,510 A | 10/2000 | Palermo |
| 6,139,524 A | 10/2000 | Killion |
| 6,176,849 B1 | 1/2001 | Yang et al. |
| 6,206,888 B1 | 3/2001 | Bicek et al. |
| 6,221,467 B1 | 4/2001 | Nazarova et al. |
| 6,238,410 B1 | 5/2001 | Vrba et al. |
| 6,254,609 B1 | 7/2001 | Vrba et al. |
| 6,287,329 B1 | 9/2001 | Duerig et al. |
| 6,322,586 B1 | 11/2001 | Monroe et al. |
| 6,330,884 B1 | 12/2001 | Kim |
| 6,331,184 B1 | 12/2001 | Abrams |
| 6,342,066 B1 | 1/2002 | Toro et al. |
| 6,355,060 B1 | 3/2002 | Lenker et al. |
| 6,375,676 B1 | 4/2002 | Cox |
| 6,379,365 B1 | 4/2002 | Diaz |
| 6,380,457 B1 | 4/2002 | Yurek et al. |
| 6,391,050 B1 | 5/2002 | Broome |
| 6,398,802 B1 | 6/2002 | Yee |
| 6,425,898 B1 | 7/2002 | Wilson et al. |
| 6,508,803 B1 | 1/2003 | Horikawa et al. |
| 6,514,228 B1 | 2/2003 | Hamilton et al. |
| 6,514,261 B1 | 2/2003 | Randall et al. |
| 6,544,278 B1 | 4/2003 | Vrba et al. |
| 6,576,006 B2 | 6/2003 | Limon et al. |
| 6,589,251 B2 | 7/2003 | Yee et al. |
| 6,602,226 B1 | 8/2003 | Smith et al. |
| 6,613,014 B1 | 9/2003 | Chi |
| 6,626,934 B2 | 9/2003 | Blaeser et al. |
| 6,669,716 B1 | 12/2003 | Gilson et al. |
| 6,709,667 B1 | 3/2004 | Lowe et al. |
| 6,726,712 B1 | 4/2004 | Raeder-Devens et al. |
| 6,726,714 B2 | 4/2004 | DiCaprio et al. |
| 6,736,839 B2 | 5/2004 | Cummings |
| 6,755,855 B2 | 6/2004 | Yurek et al. |
| 6,773,446 B1 | 8/2004 | Dwyer et al. |
| 6,776,791 B1 | 8/2004 | Stallings et al. |
| 6,802,849 B2 | 10/2004 | Blaeser et al. |
| 6,860,898 B2 | 3/2005 | Stack et al. |
| 6,939,352 B2 | 9/2005 | Buzzard et al. |
| 6,942,682 B2 | 9/2005 | Vrba et al. |
| 6,951,675 B2 | 10/2005 | Chin et al. |
| 7,001,423 B2 | 2/2006 | Euteneuer et al. |
| 7,387,640 B2 | 6/2008 | Cummings |
| 7,632,296 B2 | 12/2009 | Malewicz |
| 7,740,652 B2 | 6/2010 | Gerdts et al. |
| 8,128,676 B2 | 3/2012 | Cummings |
| 8,152,818 B2 | 4/2012 | Gunderson |
| 2001/0034548 A1 | 10/2001 | Vrba et al. |
| 2001/0034549 A1 | 10/2001 | Bartholf et al. |
| 2001/0037141 A1 | 11/2001 | Yee et al. |
| 2002/0052641 A1 | 5/2002 | Monroe et al. |
| 2002/0058951 A1 | 5/2002 | Fiedler |
| 2002/0082550 A1 | 6/2002 | Hamilton et al. |
| 2002/0095203 A1 | 7/2002 | Thompson et al. |
| 2002/0103525 A1 | 8/2002 | Cummings |
| 2002/0165523 A1 | 11/2002 | Chin et al. |
| 2003/0144671 A1 | 7/2003 | Brooks et al. |
| 2003/0163156 A1 | 8/2003 | Hebert et al. |
| 2003/0191516 A1* | 10/2003 | Weldon .............. A61F 2/95 623/1.12 |
| 2004/0098083 A1 | 5/2004 | Tran et al. |
| 2004/0148009 A1 | 7/2004 | Buzzard et al. |
| 2004/0215317 A1 | 10/2004 | Cummings |
| 2004/0267348 A1 | 12/2004 | Gunderson et al. |
| 2005/0027345 A1 | 2/2005 | Horan et al. |
| 2005/0080476 A1 | 4/2005 | Gunderson et al. |
| 2005/0149159 A1* | 7/2005 | Andreas .............. A61F 2/95 623/1.11 |
| 2005/0154439 A1 | 7/2005 | Gunderson |
| 2005/0182473 A1 | 8/2005 | Eidenschink et al. |
| 2005/0182475 A1 | 8/2005 | Jen et al. |
| 2005/0192657 A1 | 9/2005 | Colen et al. |
| 2005/0240254 A1 | 10/2005 | Austin |
| 2005/0256562 A1 | 11/2005 | Clerc et al. |
| 2006/0009833 A1 | 1/2006 | Chobotov et al. |
| 2006/0030923 A1 | 2/2006 | Gunderson |
| 2006/0041302 A1 | 2/2006 | Malewicz |
| 2006/0074477 A1 | 4/2006 | Berthiaume et al. |
| 2006/0190069 A1 | 8/2006 | Baker-Janis et al. |
| 2006/0229697 A1 | 10/2006 | Gerdts et al. |
| 2006/0292300 A1 | 12/2006 | Tan |
| 2007/0135803 A1 | 6/2007 | Belson |
| 2007/0142894 A1 | 6/2007 | Moore et al. |
| 2007/0191865 A1 | 8/2007 | Pappas |
| 2007/0208350 A1 | 9/2007 | Gunderson |
| 2007/0282420 A1 | 12/2007 | Gunderson |
| 2008/0188920 A1 | 8/2008 | Moberg et al. |
| 2008/0208320 A1 | 8/2008 | Tan-Malecki et al. |
| 2009/0024133 A1 | 1/2009 | Keady et al. |
| 2009/0036967 A1 | 2/2009 | Cummings |
| 2009/0157162 A1 | 6/2009 | Chow et al. |
| 2009/0192584 A1 | 7/2009 | Gerdts et al. |
| 2010/0256727 A1 | 10/2010 | Gerdts et al. |

FOREIGN PATENT DOCUMENTS

| | | |
|---|---|---|
| EP | 0775470 A1 | 5/1997 |
| EP | 0633756 B1 | 2/1998 |
| EP | 0820259 B1 | 2/2003 |
| EP | 1385450 B1 | 3/2007 |
| WO | 9717899 A1 | 5/1997 |
| WO | 9949808 A1 | 10/1999 |

(56) References Cited

FOREIGN PATENT DOCUMENTS

| | | | |
|---|---|---|---|
| WO | 0018330 | A1 | 4/2000 |
| WO | 0023139 | A1 | 4/2000 |
| WO | 0027309 | A1 | 5/2000 |
| WO | 0067828 | A1 | 11/2000 |
| WO | 0071059 | A1 | 11/2000 |
| WO | 0176676 | A2 | 10/2001 |
| WO | 02056953 | A2 | 7/2002 |
| WO | 2004098692 | A1 | 11/2004 |
| WO | 2005020856 | A2 | 3/2005 |
| WO | 2005107644 | A1 | 11/2005 |
| WO | 2005112824 | A1 | 12/2005 |
| WO | 2006036472 | A1 | 4/2006 |
| WO | 2007084370 | A1 | 7/2007 |

* cited by examiner

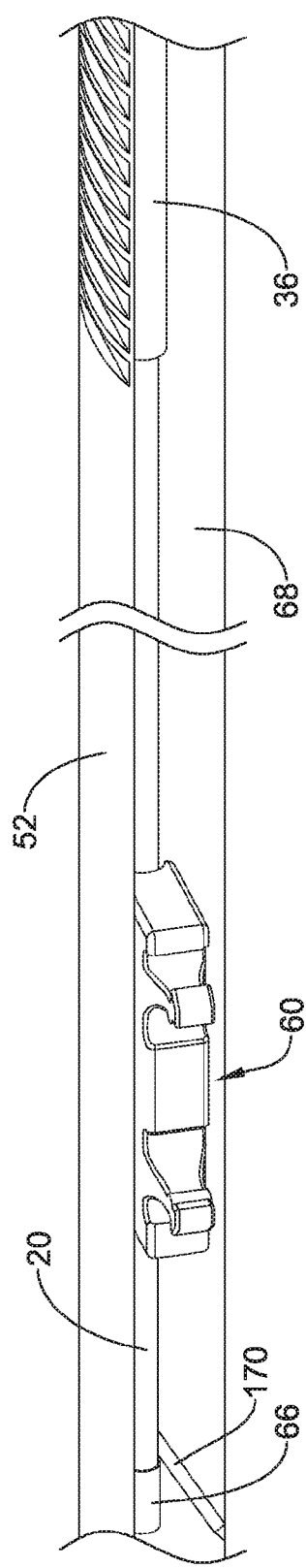

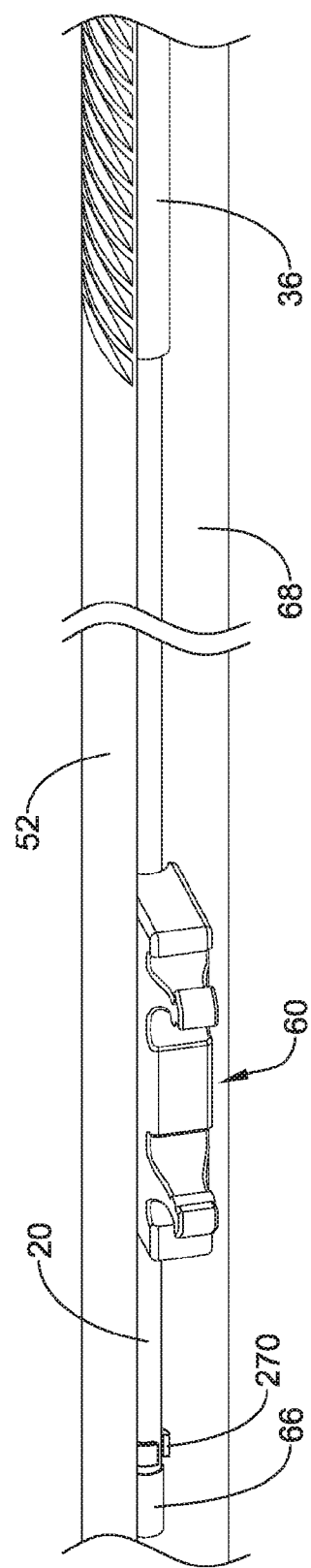

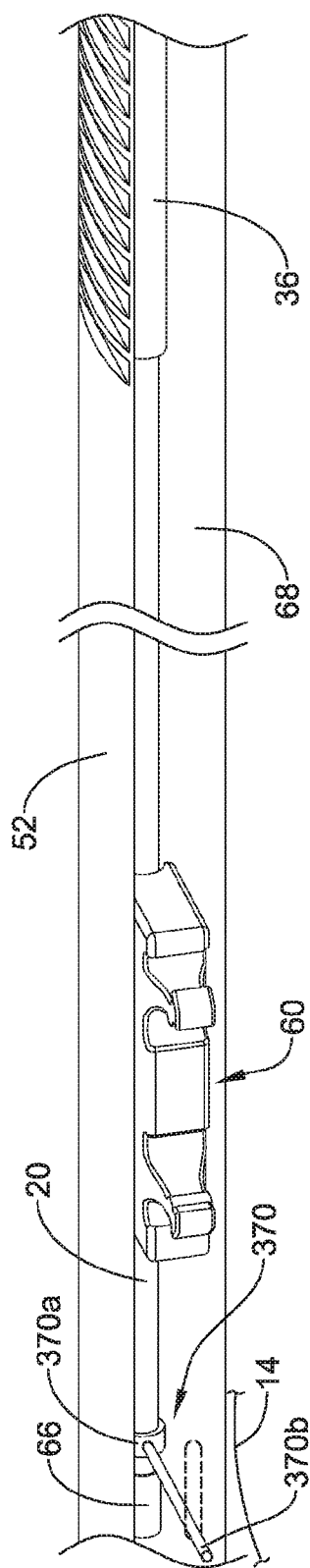

STENT DELIVERY SYSTEM

CROSS-REFERENCE TO RELATED APPLICATIONS

This application is a continuation of U.S. application Ser. No. 13/240,765, filed Sep. 22, 2011 which claims the benefit of U.S. Provisional Application Ser. No. 61/414,858, filed Nov. 17, 2010, the entire disclosure of which is incorporated herein by reference. This application is also related to U.S. Patent Application No. 61/414,835, filed on Nov. 17, 2010, the entire disclosure of which is herein incorporated by reference.

TECHNICAL FIELD

The present invention pertains to medical devices and methods for making and using medical devices. More particularly, the present invention pertains to stent delivery systems.

BACKGROUND

A wide variety of intracorporeal medical devices have been developed for medical use, for example, intravascular use. Some of these devices include stent delivery systems. These devices are manufactured by any one of a variety of different manufacturing methods and may be used according to any one of a variety of methods. Of the known stent delivery devices and methods for making and using the same, each has certain advantages and disadvantages. There is an ongoing need to provide alternative stent delivery devices as well as alternative methods for making and using stent delivery devices.

BRIEF SUMMARY

The invention provides design, material, manufacturing method, and use alternatives for stent delivery systems including self-expanding stent delivery systems and methods for making and using the same. Stent delivery systems and methods for making and using the same are disclosed. An example stent delivery system may include an inner member having a proximal end. A sleeve may be coupled to the inner member adjacent to the proximal end. A deployment sheath may be disposed about the inner member. A gear rack assembly may be coupled to the deployment sheath. A stent may be disposed between the inner member and the deployment sheath. A handle may be coupled to the inner member and to the deployment sheath. The handle may include an actuation member. The actuation member may be coupled to the gear rack assembly so that actuation of the actuation member shifts the longitudinal position of the gear rack assembly and the deployment sheath. An engagement mechanism may be coupled to the gear rack assembly. The engagement mechanism may be configured to engage the sleeve of the inner member so that proximal retraction of the gear rack assembly results in proximal retraction of the inner shaft.

Another example stent delivery system may include an inner member having an enlarged proximal end and an atraumatic distal tip. A stent may be disposed about the inner member. A deployment sheath may be disposed about the inner member and the stent. A gear rack assembly may be coupled to the deployment sheath. A handle may be coupled to the inner member and to the deployment sheath. The handle may include a thumbwheel that is coupled to the gear rack assembly so that rotation of the thumbwheel proximally retracts the gear rack assembly and the deployment sheath. An engagement mechanism may be coupled to the gear rack assembly. The engagement mechanism may be configured to catch on the enlarged proximal end of the inner member after the deployment sheath is proximally retracted a distance, and proximally retract the inner member.

An example method for deploying a stent may include providing a stent delivery system. The stent delivery system may include an inner member having an enlarged proximal end and an atraumatic distal tip. A stent may be disposed about the inner member. A deployment sheath may be disposed about the inner member and the stent. A gear rack assembly may be coupled to the deployment sheath. A handle may be coupled to the inner member and to the deployment sheath. The handle may include a thumbwheel that is coupled to the gear rack assembly so that rotation of the thumbwheel proximally retracts the gear rack assembly and the deployment sheath. An engagement mechanism may be coupled to the gear rack assembly. The engagement mechanism may be configured to catch on the enlarged proximal end of the inner member, after the deployment sheath is proximally retracted a first distance, and proximally retract the inner member. The method may also include advancing the stent delivery system through a body lumen to a position adjacent to an area of interest and rotating the thumbwheel to proximally retract the gear rack assembly the first distance. Retraction of the gear rack assembly the first distance may result in the engagement mechanism catching on the enlarged proximal end of the inner member. The method may also include further rotating the thumbwheel to further proximally retract the gear rack assembly and to proximally retract the inner member.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 14 is a side view of a portion of another example stent delivery system;

FIG. 15 is a side view of a portion of another example stent delivery system; and FIG. 16 is a side view of a portion of another example stent delivery system.

Figure 1:
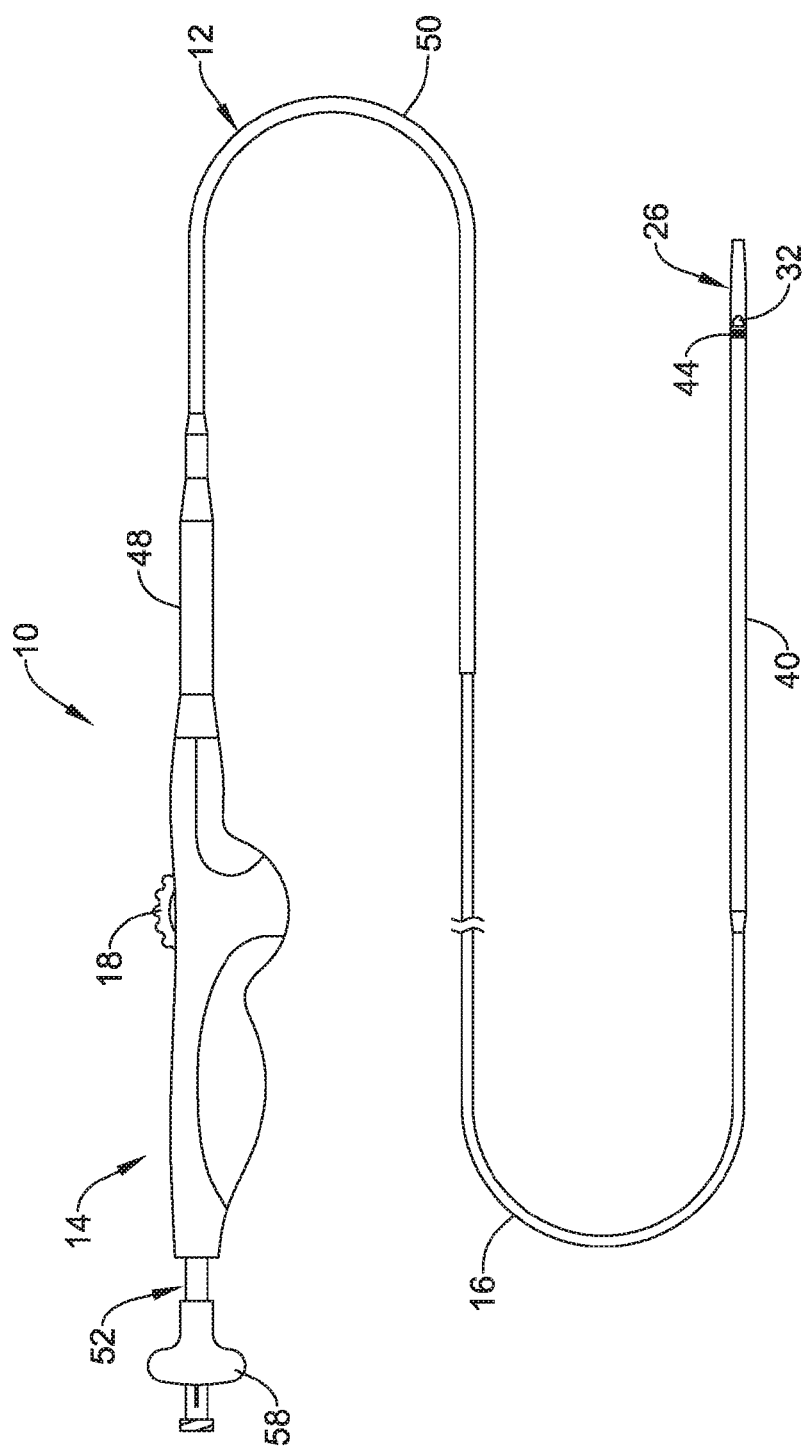
FIG. 1 is a partial cross-sectional side view of an example stent delivery system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example stent delivery system 10. System 10 may include an elongate shaft 12 and a handle 14 coupled to shaft 12. In general, system 10 may be used to deliver a suitable stent, graft, endoprosthesis or the like to an area of interest within a body lumen of a patient. The body lumen may be a blood vessel located near the heart (e.g., within or near a cardiac vessel), within a peripheral vessel, within a neurological vessel, or at any other suitable location. Deployment of the stent may include the proximal retraction of a retraction sheath 16, which overlies the stent. Retraction of sheath 16 may include the actuation of an actuation member 18 generally disposed at handle 14. In the example illustrated in FIG. 1, actuation member 18 is a thumb wheel that can be rotated by a clinician in order to accomplish proximal retraction of deployment sheath 16. Numerous other actuation members are contemplated. A number of other structures and features of system 10 can be seen in FIG. 1 and are labeled with reference numbers. Additional discussion of these structures can be found below.

Figure 2:
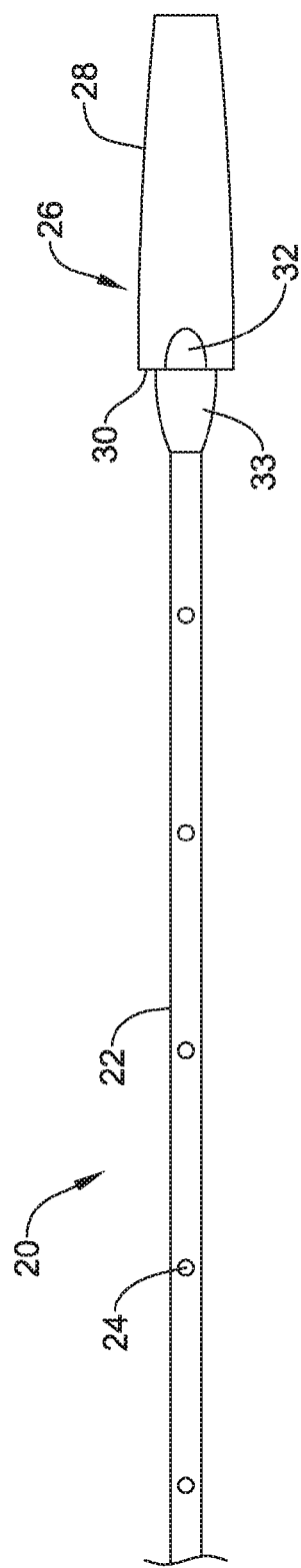
FIG. 2 is a side view of a portion of the example stent delivery system shown in FIG. 1.

FIGS. 2-6 illustrate at least some of the structural components that may be included as a part of system 10. For example, system 10 may include an inner shaft or member 20 as illustrated in FIG. 2. In at least some embodiments, inner member 20 may be a tubular structure and, thus, may include a lumen (not shown). The lumen may be a guidewire lumen that extends along at least a portion of the length of inner member 20. Accordingly, system 10 may be advanced over a guidewire to the desired target location in the vasculature. In addition, or in alternative embodiments, the lumen may be a perfusion/aspiration lumen that allows portions, components, or all of system 10 to be flushed, perfused, aspirated, or the like.

Inner member 20 may include a stent receiving region 22 about which a stent (not shown, can be seen in FIGS. 3-4) may be disposed. The length and/or configuration of stent receiving region 22 may vary. For example, stent receiving region 22 may have a length sufficient for the stent to be disposed thereon. It can be appreciated that as the length of the stent utilized for system 10 increases, the length of stent receiving region 22 also increases.

Along or otherwise disposed adjacent stent receiving region 22 may be one or more perfusion ports 24. Ports 24 may extend through the wall of inner member 20 such that fluid may be infused through the lumen of inner member 20 and may be flushed through ports 24. This may be desirable for a number of reasons. For example, ports 24 may allow a clinician to evacuate air bubbles that may be trapped adjacent the stent by perfusing fluid through ports 24. In addition, ports 24 may be used to aspirate fluid that may be disposed along inner member 20. Ports 24 may also aid in sterilization and/or other preparatory processing steps that may be involved in preparing system 10 for sale.

A tip 26 may be attached to or otherwise disposed at the distal end of inner member 20. Tip 26 may generally have a rounded or smooth shape that provides a generally atraumatic distal end to system 10. For example, tip 26 may have a smooth tapered distal portion 28 that gently tapers. Tip may also include a proximal ridge 30 that is configured so that sheath 16 can abut therewith. Tip 26 may also include a tapered proximal portion 33. Numerous other shapes and/or configurations are contemplated for tip 26.

Tip 26 may also include one or more cutouts or flats 32 formed therein. For the purposes of this disclosure, flats 32 are understood to be cutouts or flattened portions of tip 26 where the outer dimension or profile of tip 26 is reduced. The name "flats" comes from the fact that these regions may have a somewhat "flat" appearance when compared to the remainder of tip 26, which generally may have a rounded profile. The shape, however, of flats 32 is not meant to be limited to being flat or planar as numerous shapes are contemplated.

Flats 32 may allow for a gap or space to be defined between inner member 20 and deployment sheath 16 when sheath 16 abuts proximal ridge 30 of tip 26. This gap may allow for fluid, for example perfusion fluid passed through ports 24, to flow out from sheath 16. Thus, flats 32 may be used in conjunction with ports 24 to allow portions or all of system 10 to be flushed or otherwise evacuated of air bubbles.

Figure 3:
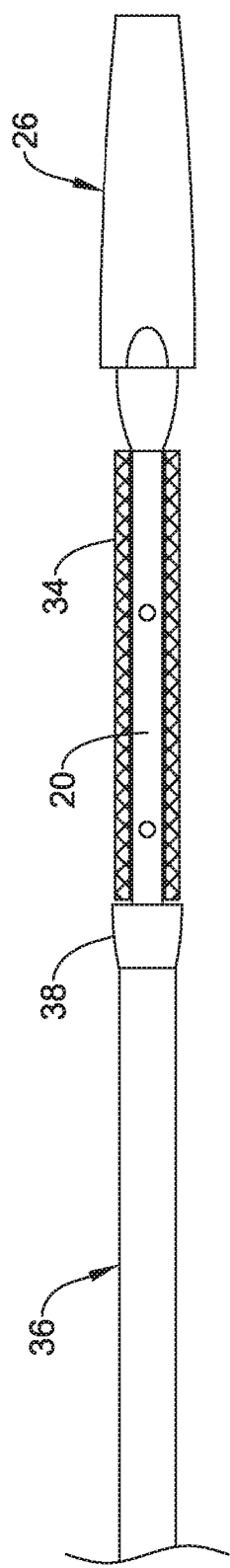
FIG. 3 is a side view of another portion of the example stent delivery system shown in FIG. 1.

FIG. 3 illustrates inner member 20 with some additional structure of system 10. In this figure, a stent 34 is disposed about inner member 20 (e.g., about stent receiving region 22 of inner member 20). In some embodiments, stent 34 is a self-expanding stent. Accordingly, stent 34 may be biased to outwardly expand. Because of this, stent 34 may not be "loaded onto" inner member 20 in a strict sense but rather may be thought of as being disposed about or surrounding inner member 20. Stent 34 may then be restrained within deployment sheath 16. In alternative embodiments, however, stent 34 may be directly loaded onto inner member 20 via crimping or any other suitable mechanical holding mechanism.

An intermediate tube 36 may also be disposed over inner member 20. In at least some embodiments, intermediate tube 36 may extend from a position adjacent to the proximal end of inner member 20 to a position proximal of the distal end of inner member 20. Intermediate tube 36 may include a bumper 38. In practice, bumper 38 may function by preventing any unwanted proximal movement of stent 38 during navigation and/or deployment of stent 14.

Bumper 38 may have any suitable form. In some embodiments, bumper 38 may be defined by a relatively short tube or sleeve that is disposed about intermediate tube 36. The material utilized for the sleeve may be the same or different from that of intermediate tube 36. Intermediate tube 36 may have a tapered or otherwise smooth transition in outer diameter adjacent bumper 38. For example, polymeric material may be disposed or reflowed adjacent bumper 38 (which may include disposing the polymeric material about a portion or all of bumper 38) so as to define a gentle transition in outer diameter at bumper 38. Other configurations are contemplated and may be utilized in alternative embodiments.

Figure 4:
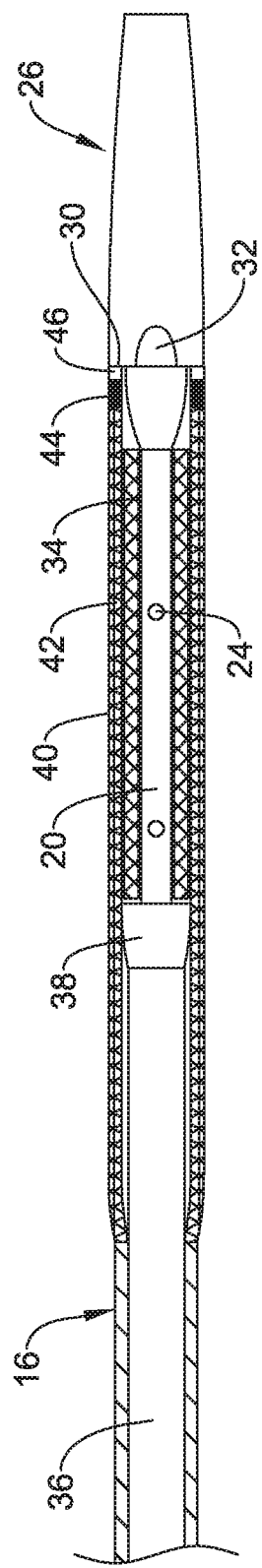
FIG. 4 is a side view of another portion of the example stent delivery system shown in FIG. 1.

FIG. 4 illustrates additional structure of system 10. Here deployment sheath 16 can be seen disposed over inner member 20, intermediate tube 36, and stent 34. It can be appreciated that sheath 16 is configured to shift between a first position, for example as shown in FIG. 4, where sheath 16 overlies stent 34 and a second position where sheath 16 is proximally retracted to a position substantially proximal of stent 34. In general, the first position may be utilized during navigation of system 10 to the appropriate location within a body lumen and the second position may be used to deploy stent 34.

Sheath 16 may include a flared portion 40 where the outer diameter of sheath 16 is increased. In portion 40, the thickness of the tubular wall of sheath 16 may or may not be increased. Flared portion 40 may be desirable for a number of reasons. For example, flared portion 40 may allow sheath 16 to have an adequate inner dimension that is suitable so that sheath 16 may be disposed about stent 34 and bumper 38.

In at least some embodiments, sheath 16 may include a reinforcing member 42 embedded or otherwise included therewith. Reinforcing member 42 may have any number of a variety of different configurations. For example, reinforcing member 42 may include a braid, coil, mesh, combinations thereof, or the like, or any other suitable configuration. In some embodiments, reinforcing member 42 may extend along the entire length of sheath 16. In other embodiments, reinforcing member 42 may extend along one or more portions of the length of sheath 16. For example, reinforcing member 42 may extend along flared portion 40.

Sheath 16 may also include a radiopaque marker or band 44. In general, marker band 44 may be disposed adjacent to the distal end 46 of sheath 16. One or more additional marker bands 44 may be disposed along other portions of sheath 16 or other portions of system 10. Marker band 44 may allow the distal end 46 of sheath 16 to be fluoroscopically visualized during advancement of system 10 and/or deployment of stent 34.

FIG. 4 also illustrates the distal end 46 of sheath 16 abutting proximal ridge 30. In this configuration, stent 34 can be flushed (e.g., to remove air bubbles) by infusing fluid through inner member 20 and through ports 24. Because of flats 32, fluid may be allowed to be flushed out of sheath 16 by passing through the gaps formed between inner member 20 and sheath 16 at flats 32.

Figure 5:
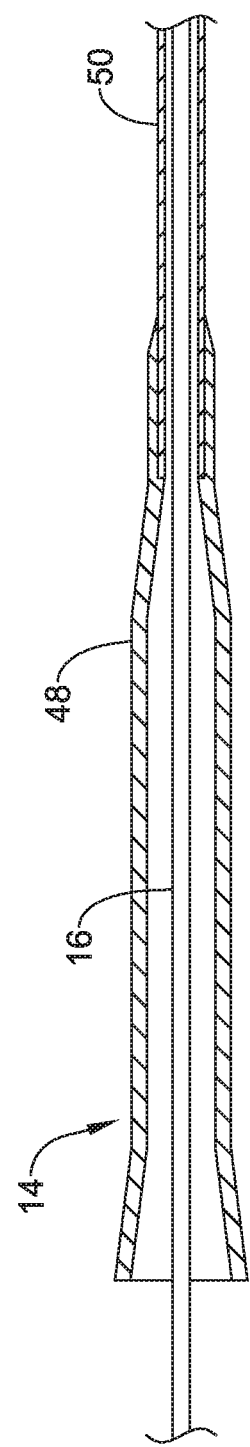
FIG. 5 is a side view of another portion of the example stent delivery system shown in FIG. 1.

FIG. 5 illustrates a distal portion 48 of handle 14. Here it can be seen that handle 14 is attached to an outer member 50. Outer member 50 may be disposed about sheath 16 and extend along a portion of the length of sheath 16. Thus, along at least a portion of the length of system 10, system 10 may include four tubular structures that may be coaxially arranged—namely outer member 50, deployment sheath 16, intermediate tube 36, and inner member 20. In at least some embodiments, outer member 50 may provide system 10 with a number of desirable benefits. For example, outer member 50 may include or otherwise be formed from a lubricious material that can reduce friction that may be associated with proximally retracting sheath 16. In addition, outer member 50 may comprise a surface that can be clamped or otherwise locked so that the position of system 10 can be maintained without negatively impacting the retraction of sheath 16 (which might otherwise be impacted if sheath 16 was to be clamped). Numerous other desirable benefits may also be achieved through the use of outer member 50.

Figure 6:
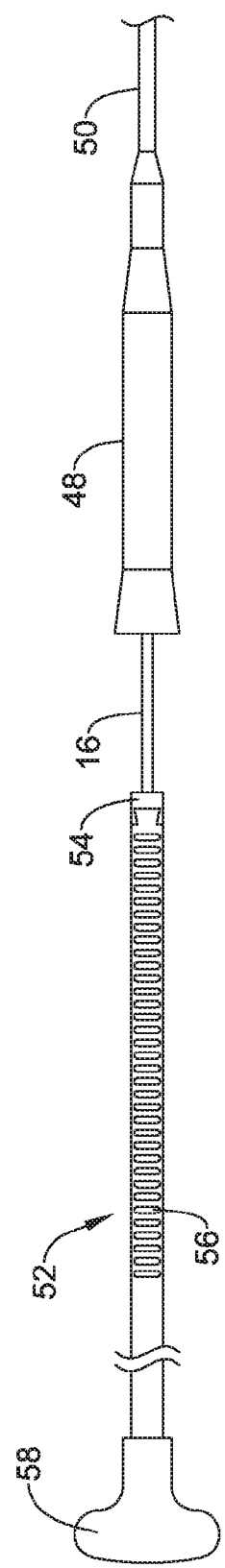
FIG. 6 is a side view of another portion of the example stent delivery system shown in FIG. 1.

Sheath 16 may pass proximally through outer member 50 and extend proximally back within handle 14. Intermediate tube 36 and inner member 20 both also extend back within handle 14 and are disposed within sheath 14. The proximal end of sheath 16 may be attached to a gear rack assembly 52 with a fastener or clip 54 as illustrated in FIG. 6. Thus, it can be appreciated that proximal movement of gear rack assembly 52 may result in analogous proximal movement of deployment sheath 16. Gear rack assembly 52 may include a plurality of teeth or gears 56. In practice, teeth 56 may be configured to engage with corresponding teeth or gears (not shown) on thumbwheel 18. Consequently, rotation of thumbwheel 18, via gearing thereof with gears 56, can be utilized to proximally retract gear rack assembly 52 and, thus, sheath 16. Other structural arrangements may be utilized to accomplish proximal retraction of gear rack assembly 52 through the actuation of thumbwheel 18 or any other suitable actuation member.

Gear rack assembly 52 may also include a flared proximal end 58. When properly assembly, the main body of gear rack assembly 52 may be disposed within handle 14 and proximal end 58 may be disposed along the exterior of handle 14. Gear rack assembly 52 may have a slot or groove 68 formed therein (not shown in FIG. 6, can be seen in FIG. 8). Groove 68 may extend the length of gear rack assembly 52, including extending along proximal end 58. Because proximal end 58 may be generally located near the proximal end of inner member 20, the flared shape of proximal end 58 and the orientation of groove 68 may allow proximal end 58 to function as a guidewire introducer or funnel that may assist a clinician in placing, holding, removing, and/or exchanging a guidewire extending through inner member 20.

Figure 7:
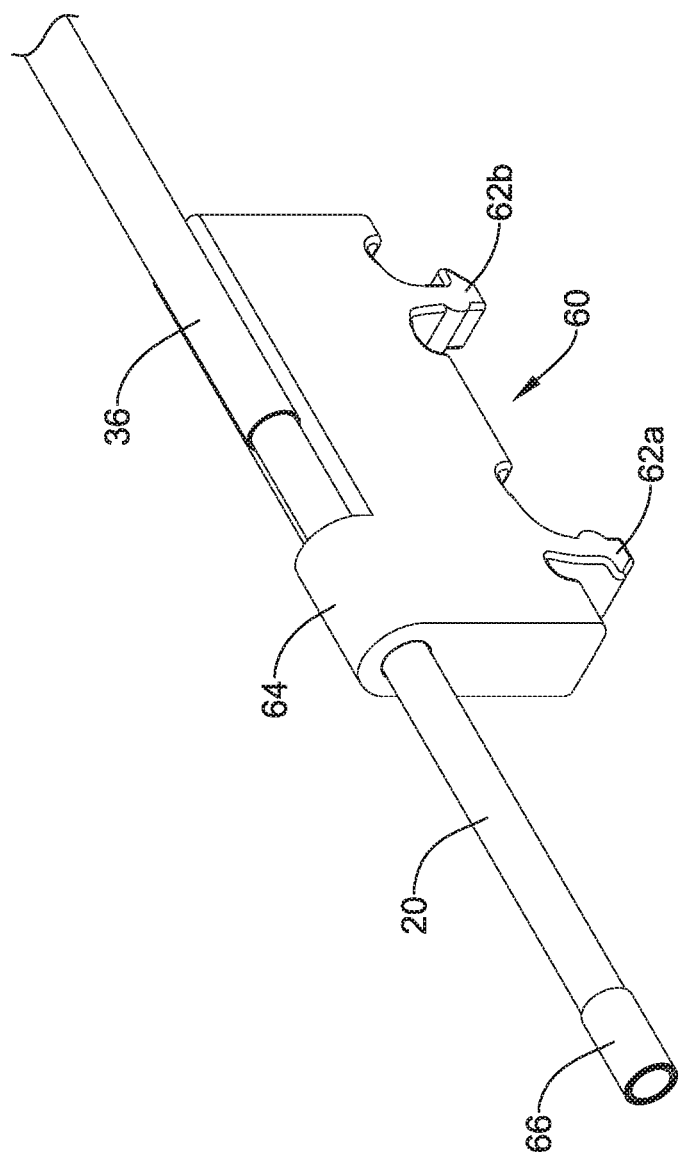
FIG. 7 is a perspective view of another portion of the example stent delivery system shown in FIG. 1.

In order to properly deploy stent 34, the various components of system 10 may need to work in concert so that relative motion of sheath 16 can be accomplished relative to inner member 20. In addition, to improve the accuracy of deployment, intermediate tube 36 may need to be configured so as to provide the desired longitudinal support necessary to limit proximal movement of stent 34. In at least some embodiments, the proper configuration of these structures may be maintained, at least in part, through the use of a clip member 60 as illustrated in FIG. 7.

In general, clip member 60 is disposed within handle 14 and is configured to be secured along the interior of handle 14. Accordingly, clip member 60 allows the longitudinal position of one or more portions of system 10 to be fixed relative to handle 14. In order to secure clip member 60 to handle 14, clip member 60 may include one or more fasteners or legs 62a/62b. For example, handle 14 may have one or more slots, grooves, openings, or the like that are configured to seat legs 62a/62b such that the relative position of clip member 60 relative to handle 14 is fixed. In some embodiments, clip member 60 may be configured to "snap in" to handle 14. This may desirably simplify manufacturing.

The orientation of clip member 60 may be such that it is positioned near one or more structures of system 10. In at least some embodiments, clip member 60 may be configured so that at least a portion thereof is positioned within a groove 68 (not shown in FIG. 7, can be seen in FIG. 8) of gear rack assembly 52. This may desirably place clip member 60 near inner member 20 and intermediate tube 36 (which may also extend through groove 68) such that clip member 60 can be associated therewith.

Inner member 20 may be coupled with clip member 60 such that the longitudinal position of inner member 20 can be fixed relative to handle 14. For example, clip member 60 may include one or more tubular sections, for example a tubular section 64, through which inner member 20 may extend. In some embodiments, a sleeve or cuff 66 may be disposed about inner member 20 at a position proximal of the proximal end of clip member 60. Sleeve 66 may substantially prevent any unwanted distal movement of inner member 20 via interference with clip member 60.

When stent 34 is deployed, a clinician may actuate the actuation thumbwheel 18. Because of the association of thumbwheel 18 with gear rack assembly 52, relative rotation of thumbwheel 18 causes proximal movement of deployment sheath 16. As deployment sheath 16 proximally retracts, stent 34 is "uncovered" and (if stent 34 is a self-expanding stent) can expand within the body lumen.

In typical stent delivery systems, the relative position of the inner member or structure (e.g., the structure about which the stent is disposed or is loaded on) remains fixed relative to the deployment sheath during stent deployment. In these systems, the inner member is removed from the body lumen by proximally retracting it after the stent is fully deployed. In other words, the deployment process in typical systems generally includes: (1) proximally retracting the deployment sheath to fully deploy the stent and then (2) proximally retracting the inner member and/or other components of the system by pulling the inner member proximally through the interior of the deployed stent and, ultimately, out from the body.

Because the inner member of typical stent delivery systems may be designed to include an atraumatic tip, the proximal retracting of the inner member through the interior of the stent also includes proximally retracting the tip through the interior of the stent. Such tips may have an outer profile that approximates the outer diameter of the deployment sheath. In other words, the outer profile of the tip may be relatively "enlarged" as compared to the inner member. Because of the relatively large profile of the tip, there may be a possibility that the tip could engage the stent when being proximally retracted. This could displace the position of the stent, disrupt the structure of the stent, or have any number of undesirable effects.

Stent delivery system 10 is designed to help reduce the possibility that tip 26 could "catch" on stent 34. For example, system 10 is designed to proximally retract inner member 20 along with deployment sheath 16. This, desirably, brings tip 26 proximally during stent 34 deployment and obviates the need for the clinician to pull tip 26 back through the full length of stent 34 after deployment. In use, a clinician may actuate thumbwheel 18 to begin proximally retracting deployment sheath 16. After sheath 16 is retracted a relatively short distance, a structural feature of system 10 may interact with inner member 20 so that inner member 20 begins to also retract upon further retraction of deployment sheath 16.

Figure 8:
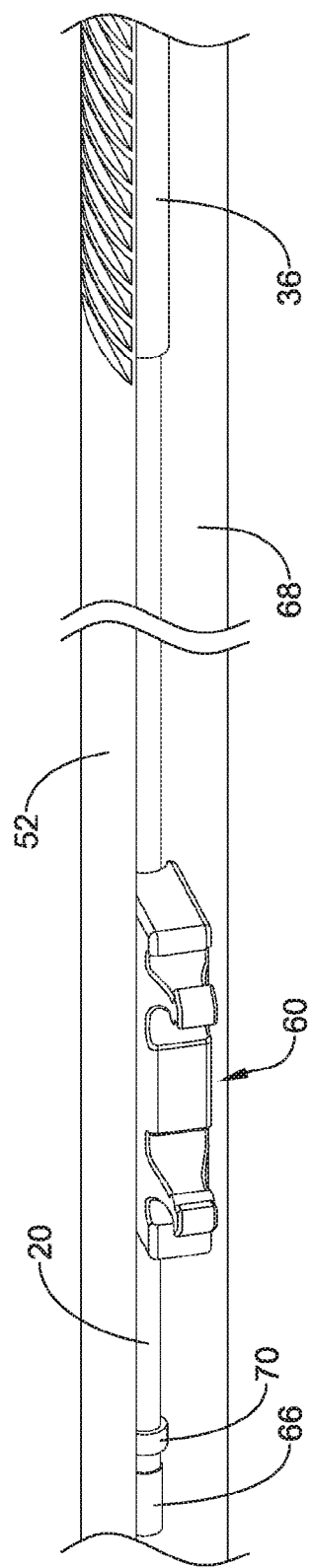
FIG. 8 is a side view of another portion of the example stent delivery system shown in FIG. 1.

In at least some embodiments, the structural feature of system that may result in proximal movement of inner member 20 includes a feature of gear rack assembly 52 (which is already associated with proximal movement of deployment sheath 16). For example, gear rack assembly 52 may include a loop or catch 70 as shown in FIG. 8. Loop 70 may be positioned a relatively short distance proximally of clip member 60.

Inner member 20 may extend through loop 70. The short distance between loop 70 and clip member 60 may allow deployment sheath 16 to begin proximally retracting to uncover stent 34 and, if stent 34 is a self-expanding stent, for stent 34 to begin expanding. However, further retraction of deployment sheath 16 will ultimately lead to loop 70 engaging sleeve 66 on inner member 20. Accordingly, any further proximal retraction of deployment sheath 16 will result in analogous proximal retraction of inner member 20 (and, thus, tip 26). During the deployment, the relative position of intermediate tube 36 remains substantially stationary. For example, intermediate tube 36 (which is shown spaced from clip member 60 in FIG. 8 but in practice will abut clip member 60) may be positioned so that it abuts clip member 60. Because clip member 60 is fixed to handle 14, intermediate tube 36 remains substantially fixed and, thus, prevents any unwanted proximal movement of stent 34 during deployment.

Figure 9:
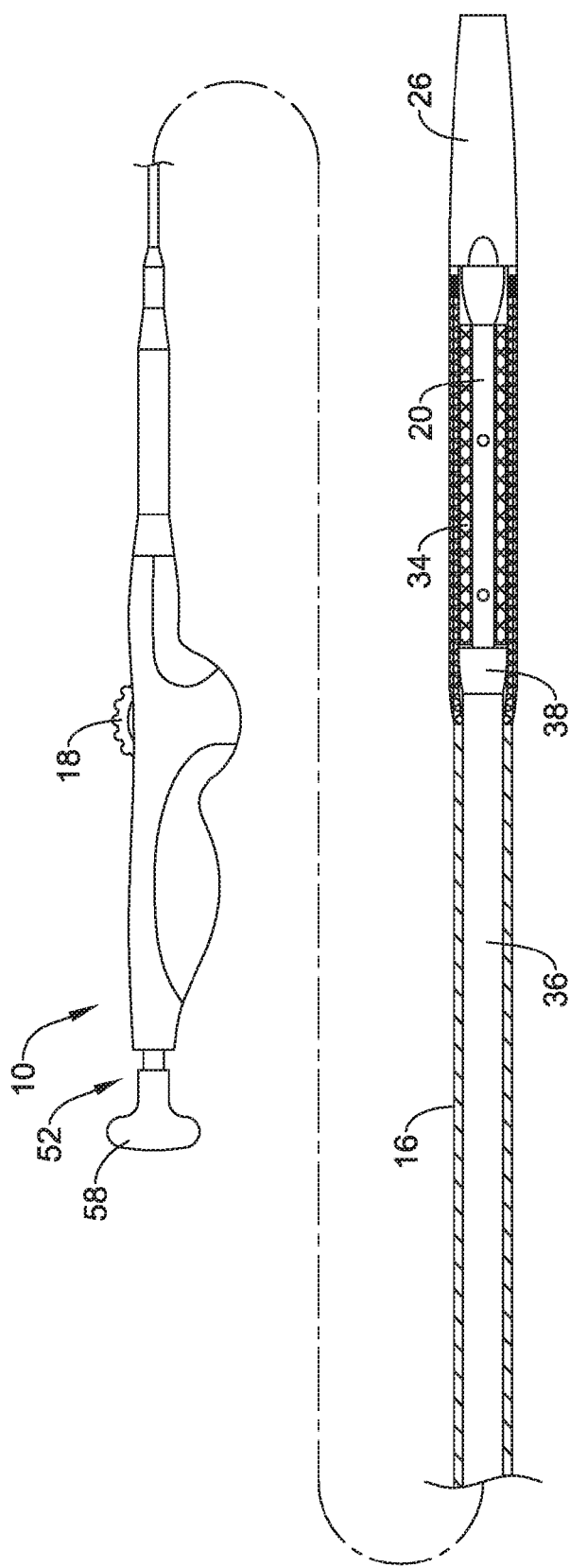
FIGS. 9-13 illustrate the use of the stent delivery system illustrated in FIG. 1.
Figure 10:
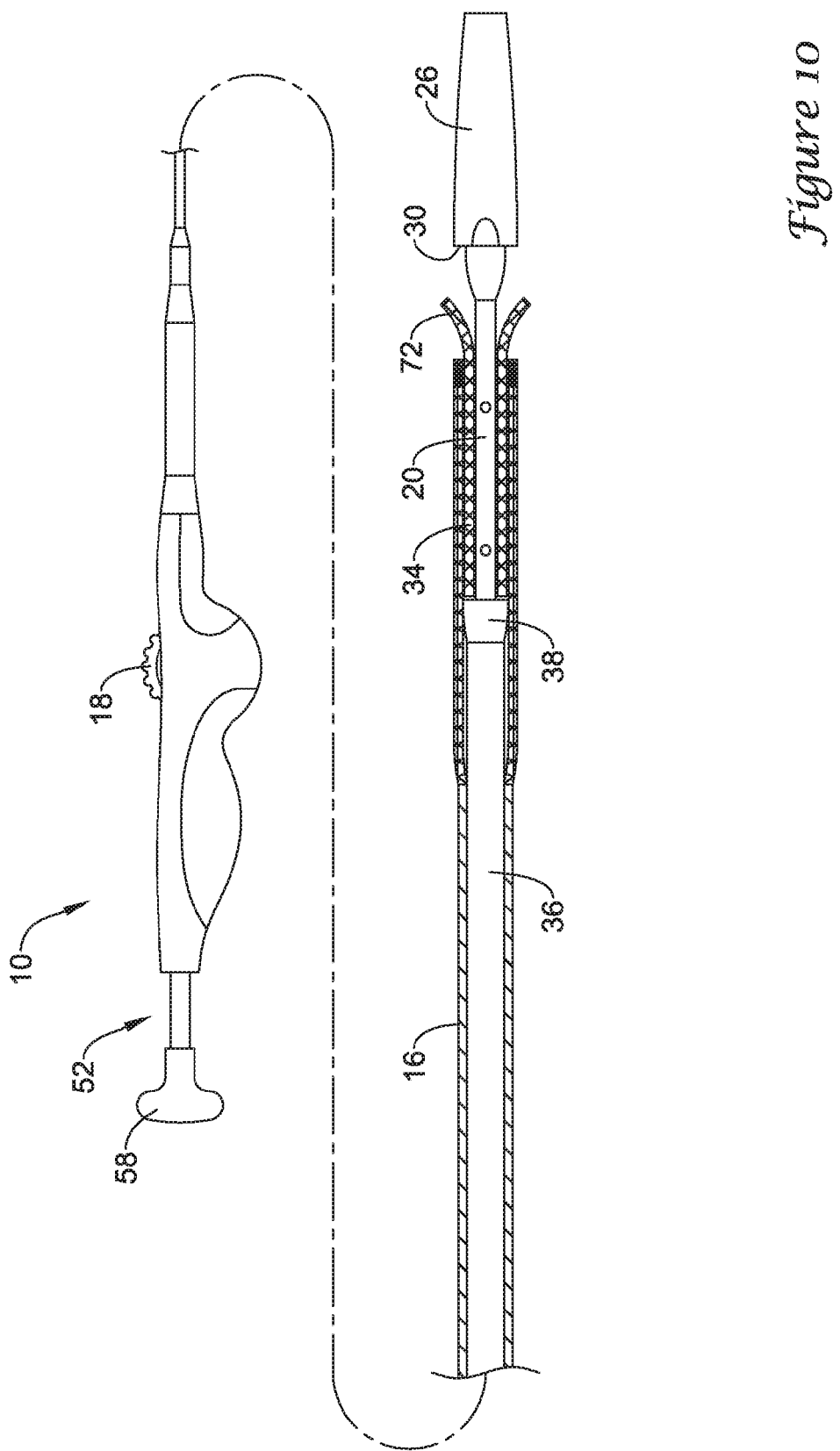
Figure 11:
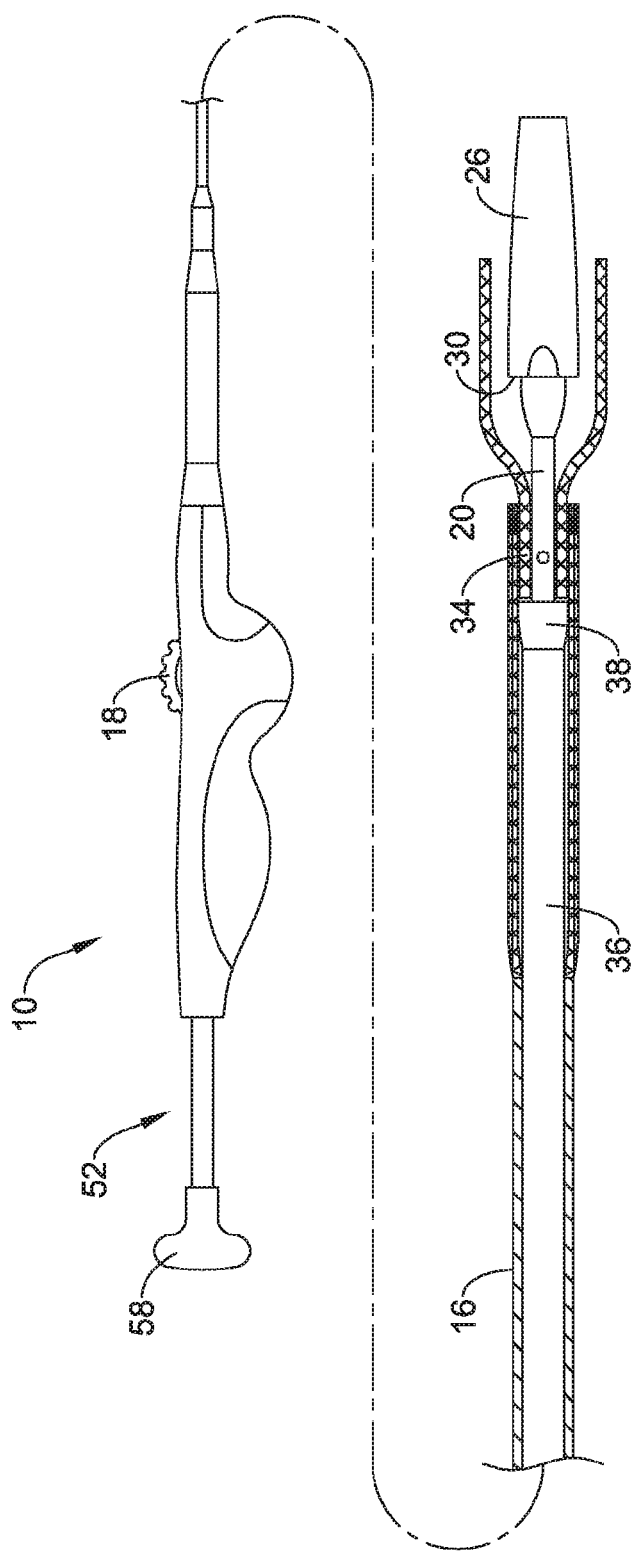
Figure 12:
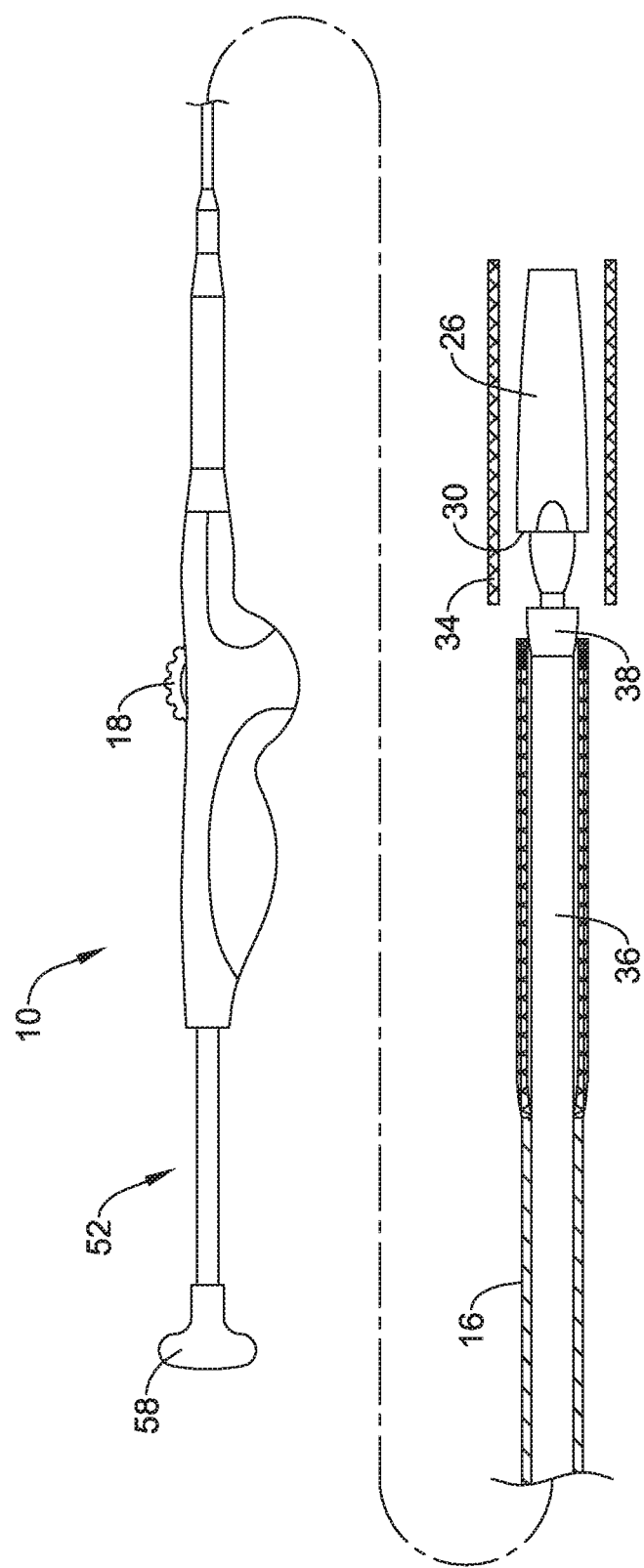
Figure 13:
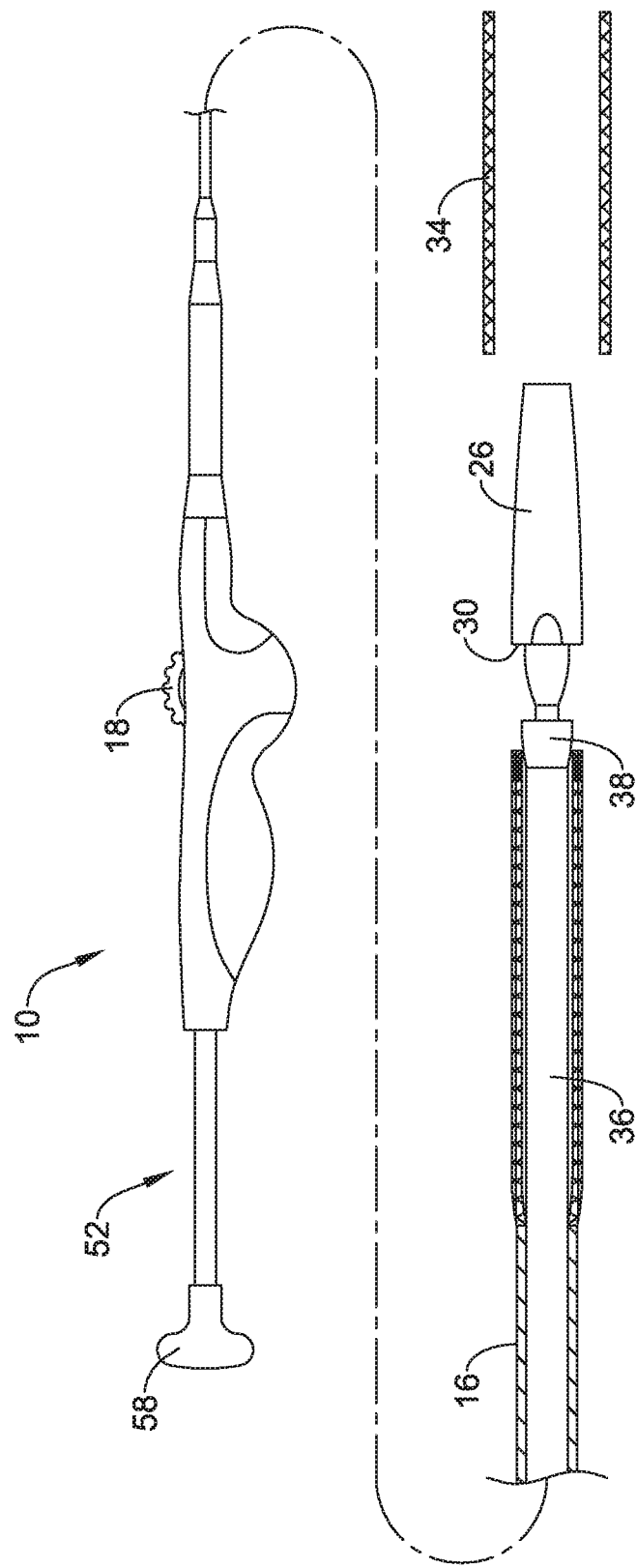

FIGS. 9-13 schematically illustrate the deployment of stent 34 with system 10. For example, FIG. 9 illustrates the relative position of the various structures of system 10 prior to deployment. With actuation of thumbwheel 18, deployment sheath 16 beings to proximally retract (via gear rack assembly 52) to uncover stent 34 as illustrated in FIG. 10. After gear rack assembly 52 is proximally retracted a distance sufficient to result in loop 70 engaging sleeve 66 of inner member 20, further proximal retraction of gear rack assembly 52 begins to also proximally retract inner member 20 and, thus, tip 26 as shown in FIG. 11. Proximal retraction may continue until the full length of stent 34 is uncovered and, thus, stent 34 is deployed as shown in FIG. 12. Because inner member 20 is proximally retracted along with deployment sheath 16, tip 26 may be positioned near the proximal end of the stent 34 at the completion of deployment. This may include positioning proximal ridge 30 of tip 26 (which may be a possible "catch point" of tip 26) at or near the proximal end of stent 34. Because of this, tip 26 only needs to travel a relatively short distance in order to clear stent 34 as shown in FIG. 13.

While the use of loop 70 may be one manner in which the structure of system 10 can proximally retract inner member 20 along with sheath 16, it can be appreciated that a variety of other structural relationships may be utilized and are contemplated. For example, FIG. 14 illustrates a portion of another example gear rack assembly 152, which can be used with system 10 as well as other systems disclosed and contemplated herein, that includes a projection 170 that can interact with sleeve 66. In this embodiment, projection 170 may project outward from the inner surface of gear rack assembly 152 (e.g., along a portion or all of the interior of groove 152). Projection 170 may be sufficiently large so that it can interfere with sleeve 66 and, thus, catch on sleeve 66 so as to proximally retract inner member 20.

FIG. 15 illustrates a portion of another example gear rack assembly 252, which can be used with system 10 as well as other systems disclosed and contemplated herein, that includes a horseshoe shaped clip 270 that can interact with sleeve 66. Clip 270 is similar to loop 70 except that clip 270 does not form a full loop of material that surrounds inner member 20. Such a configuration may be desirable for a number of reasons. For example, clip 270 may allow assembly of system 10 to include snapping inner member 20 into clip 270 rather than feeding inner member 20 through a complete loop structure. Other forms, shapes, and configurations are contemplated for clip 270.

FIG. 16 illustrates a portion of another example gear rack assembly 352, which can be used with system 10 as well as other systems disclosed and contemplated herein, that includes a loop assembly 370 that can interact with sleeve 66. Loop assembly 370 may include loop 370*a* and a rod 370*b* that may be accessible along the exterior of handle 14 so that a user can manipulate the position of inner member 20 manually. It should be noted that loop 370*a* may be complete loop (e.g., similar to loop 70) or a partial loop (e.g., similar to clip 270). Other forms and configurations are contemplated for loop assembly 370.

The materials that can be used for the various components of system 10 (and/or other systems disclosed herein) may include those commonly associated with medical devices. For simplicity purposes, the following discussion makes reference to shaft 12, deployment sheath 16, and inner member 20. However, this is not intended to limit the invention as the discussion may be applied to other similar members and/or components of members or systems disclosed herein.

Shaft 12, deployment sheath 16, and inner member 20, and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12, deployment sheath 16, and inner member 20 may also be doped with, made of, or otherwise include a radiopaque material including those listed herein or other suitable radiopaque materials.

In some embodiments, a degree of MRI compatibility is imparted into system 10. For example, to enhance compatibility with Magnetic Resonance Imaging (MRI) machines, it may be desirable to make shaft 12, deployment sheath 16, and inner member 20, in a manner that would impart a degree of MRI compatibility. For example, shaft 12, deployment sheath 16, and inner member 20, or portions thereof, may be made of a material that does not substantially distort the image and create substantial artifacts (artifacts are gaps in the image). Certain ferromagnetic materials, for example, may not be suitable because they may create artifacts in an MRI image. Shaft 12, deployment sheath 16, and inner member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form shaft 12, deployment sheath 16, and inner member 20, and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery system, comprising:
    an inner member having a proximal end;
    a sleeve coupled to the inner member adjacent to the proximal end;
    a deployment sheath disposed about the inner member;
    a bumper member disposed between the inner member and the deployment sheath;
    wherein the bumper member comprises an intermediate tube disposed between the inner member and the deployment sheath;
    a gear rack assembly coupled to the deployment sheath;
    a handle coupled to the inner member and to the deployment sheath;
    wherein the handle includes an actuation member, the actuation member being coupled to the gear rack assembly so that actuation of the actuation member shifts the longitudinal position of the gear rack assembly and the deployment sheath; and
    an engagement mechanism located along an inner groove of the gear rack assembly and coupled thereto, the engagement mechanism being configured to engage the sleeve of the inner member so that proximal retraction of the gear rack assembly results in proximal retraction of the inner shaft.

2. The stent delivery system of claim 1, further comprising a stent disposed between the inner member and the deployment sheath.

3. The stent delivery system of claim 1, wherein the engagement mechanism includes a loop extending from the gear rack assembly.

4. The stent delivery system of claim 3, wherein the engagement mechanism includes a rod extending from the loop to a position along the exterior of the handle.

5. The stent delivery system of claim 1, wherein the engagement mechanism includes a projection extending from the gear rack assembly.

6. The stent delivery system of claim 1, wherein the engagement mechanism includes a horseshoe shaped member extending from the gear rack assembly.

7. The stent delivery system of claim 1, wherein the engagement mechanism is arranged to catch on the sleeve after the deployment sheath is proximally retracted a distance.

8. The stent delivery system of claim 7, wherein the engagement mechanism is configured to proximally retract the inner member after the engagement mechanism is caught on the sleeve.

9. The stent delivery system of claim 1, wherein the actuation member includes a thumbwheel.

10. The stent delivery system of claim 1, further comprising an outer member disposed over a portion of the deployment sheath.

11. The stent delivery system of claim 1, wherein the gear rack assembly has a flared proximal end.

12. A stent delivery system, comprising:
    an inner member having an enlarged proximal end and an atraumatic distal tip;

a stent disposed about the inner member;

a deployment sheath disposed about the inner member and the stent;

an intermediate tube disposed between the inner member and the deployment sheath, the intermediate tube having a distal end disposed adjacent a proximal end of the sheath;

a gear rack assembly coupled to the deployment sheath;

a handle coupled to the inner member and to the deployment sheath;

wherein the handle includes a thumbwheel that is coupled to the gear rack assembly so that rotation of the thumbwheel proximally retracts the gear rack assembly and the deployment sheath; and an engagement mechanism coupled to an inner groove of the gear rack assembly, the engagement mechanism being configured to catch on the enlarged proximal end of the inner member, after the deployment sheath is proximally retracted a distance, and proximally retract the inner member.

13. The stent delivery system of claim 12, wherein the engagement mechanism includes a loop extending from the gear rack assembly.

14. The stent delivery system of claim 13, wherein the engagement mechanism includes a rod extending from the loop to a position along the exterior of the handle.

15. The stent delivery system of claim 12, wherein the engagement mechanism includes a projection extending from the gear rack assembly.

16. The stent delivery system of claim 12, wherein the engagement mechanism includes a horseshoe shaped member extending from the gear rack assembly.

17. The stent delivery system of claim 12, further comprising an outer member disposed over a portion of the deployment sheath.

18. A stent delivery system, comprising:

an inner member having an atraumatic distal tip;

a stent disposed about the inner member;

a deployment sheath disposed about the inner member and the stent;

an intermediate tube disposed between the inner member and the deployment sheath;

a gear rack assembly coupled to the deployment sheath; and a handle coupled to the inner member and to the deployment sheath, the handle including a thumbwheel;

wherein rotation of the thumbwheel causes the gear rack assembly and deployment sheath to retract proximally; and wherein further rotation of the thumbwheel also causes the inner member to retract proximally along with the deployment sheath.

* * * * *